(12) United States Patent
Sarron et al.

(10) Patent No.: US 11,628,399 B2
(45) Date of Patent: *Apr. 18, 2023

(54) SYSTEM FOR SEPARATING GAS (71) Applicant: CRI, ehf, Kópavogur (IS)

(72) Inventors: Emeric Sarron, Kópavogur (IS); Húni Sighvatsson, Kópavogur (IS); Ásgeir Ívarsson, Kópavogur (IS)

(73) Assignee: CRI, EHF, Kopavogur (IS)

( * ) Notice: Subject to any disclaimer, the term of this patent is extended or adjusted under 35 U.S.C. 154(b) by 132 days.

This patent is subject to a terminal disclaimer.

(21) Appl. No.: 17/197,306

(22) Filed: Mar. 10, 2021

(65) Prior Publication Data
US 2021/0197121 A1    Jul. 1, 2021

Related U.S. Application Data

(63) Continuation of application No. 16/208,870, filed on Dec. 4, 2018, now Pat. No. 10,960,349.
(Continued)

(51) Int. Cl.
*B01D 5/00* (2006.01)
*B01D 53/62* (2006.01)
(Continued)

(52) U.S. Cl.
CPC ............. *B01D 53/62* (2013.01); *B01D 3/143* (2013.01); *B01D 5/0069* (2013.01);
(Continued)

(58) Field of Classification Search
CPC ........... B01D 53/1425; B01D 53/1475; B01D 53/18; B01D 53/62; B01D 53/77;
(Continued)

(56) References Cited

U.S. PATENT DOCUMENTS 2,549,290 A   4/1951  Congdon et al.
2,727,367 A   12/1955 McKinney
(Continued)

FOREIGN PATENT DOCUMENTS

CN   102719289 A   10/2012
CN   104031710 A    9/2014
(Continued)

OTHER PUBLICATIONS

KR20150019394A_ENG (Espacenet machine translation of Lee) (Year: 2015).*
(Continued)

*Primary Examiner* — Jonathan Miller
*Assistant Examiner* — Gabriel E Gitman
(74) *Attorney, Agent, or Firm* — Workman Nydegger (57) ABSTRACT

An improved system for separating gas from a process stream by providing a stripping unit at the overhead stream of a fractionation column to selectively and effectively remove the gas using a stripping fluid without providing a dedicated light-ends separations unit. The stripper unit may be connected to the reflux drum at the overhead stream. The system for separating gas further achieves greater thermodynamic efficiency by means of a split column design using mechanical vapor recompression with the reboiler and condenser integrated in a falling-film evaporator- or thermosiphon-type vapo-condenser.

18 Claims, 7 Drawing Sheets

Related U.S. Application Data (60) Provisional application No. 62/594,320, filed on Dec. 4, 2017.

(51) Int. Cl.

| | | |
|---|---|---|
| *B01D 3/14* | (2006.01) | |
| *B01D 47/02* | (2006.01) | |
| *B01D 53/77* | (2006.01) | |
| *B01D 19/00* | (2006.01) | |
| *C07C 29/151* | (2006.01) | |
| *C07C 31/04* | (2006.01) | |

(52) U.S. Cl.
CPC ......... *B01D 19/0015* (2013.01); *B01D 47/02* (2013.01); *B01D 53/77* (2013.01); *B01D 2256/10* (2013.01); *B01D 2256/12* (2013.01); *B01D 2256/16* (2013.01); *B01D 2257/504* (2013.01); *C01B 2203/0475* (2013.01); *C07C 29/151* (2013.01); *C07C 31/04* (2013.01)

(58) Field of Classification Search
CPC .................. B01D 3/143; B01D 5/0069; B01D 19/0015; B01D 3/343; B01D 3/346; B01D 47/02; B01D 2256/10; B01D 2256/12; B01D 2256/16; B01D 2257/504; C01B 2203/0475; C07C 29/76; C07C 29/151; C07C 31/04
See application file for complete search history.

(56) References Cited

U.S. PATENT DOCUMENTS

| | | | |
|---|---|---|---|
| 3,872,025 A | | 3/1975 | Singleton |
| 3,918,934 A | | 11/1975 | Kriebel et al. |
| 4,002,525 A | * | 1/1977 | Baierl .................... D21C 11/06 |
| | | | 159/49 |
| 4,372,755 A | | 2/1983 | Tolman et al. |
| 4,428,799 A | | 1/1984 | Standiford |
| 4,717,409 A | | 1/1988 | Atkinson |
| 5,346,593 A | | 9/1994 | Cialkowski et al. |
| 5,441,990 A | | 8/1995 | Robin et al. |
| 5,715,706 A | | 2/1998 | Rathbone |
| 7,470,811 B2 | | 12/2008 | Thiebaut |
| 7,479,468 B2 | | 1/2009 | Van Egmond et al. |
| 8,729,141 B2 | | 5/2014 | Bae et al. |
| 10,016,699 B2 | | 7/2018 | Wakabayashi et al. |
| 2002/0113228 A1 | | 8/2002 | Kim et al. |
| 2002/0146363 A1 | * | 10/2002 | Benderly .................. C01C 1/12 |
| | | | 423/352 |
| 2009/0077866 A1 | | 3/2009 | Kalnes et al. |
| 2009/0188867 A1 | | 7/2009 | Vuong et al. |
| 2011/0209407 A1 | | 9/2011 | Arya et al. |
| 2012/0107209 A1 | * | 5/2012 | Vera-Castaneda ........................... |
| | | | C01B 17/0408 |
| | | | 423/539 |
| 2015/0202547 A1 | | 7/2015 | Wakabayashi et al. |
| 2016/0346725 A1 | * | 12/2016 | Udatsu ............... B01D 53/1418 |
| 2017/0320796 A1 | | 11/2017 | Lee et al. |
| 2018/0119023 A1 | | 5/2018 | Eizenga et al. |

FOREIGN PATENT DOCUMENTS

| | | | | |
|---|---|---|---|---|
| CN | 104208983 A | | 12/2014 | |
| CN | 205803360 U | | 12/2016 | |
| EP | 2831025 B1 | | 8/2017 | |
| FR | 2583988 A1 | | 1/1987 | |
| GB | 2158435 A | | 11/1985 | |
| KR | 20150019394 A | * | 2/2015 | ............. B01D 53/14 |
| KR | 20150086198 A | | 7/2015 | |
| WO | 2007108014 A1 | | 9/2007 | |
| WO | 2013144041 A1 | | 10/2013 | |

OTHER PUBLICATIONS

Xu et al., "Process Analysis of Methanol Distillation," Beijing Aerospace Wanyuan Coal Chemical Engineering Technology Co., Ltd., vol. 39, No. 11, 15 Pages.
Office Action from corresponding Chinese Application No. 2018800286594, dated Mar. 17, 2021.
International Search Report from PCT Application No. PCT/IB2018/059633, dated Feb. 25, 2019.
Al-Kalbani et al.,"Comparative Energetic Assessment of Methanol Production from CO2: Chemical Versus Electrochemical Process", Applied Energy vol. 165, Dec. 28, 2015, 13 pages.
Pérez-Fortes et al., "Methanol Synthesis Using Captured CO2 as Raw Material: Techno-Economic and Environmental Assessment", Applied Energy, vol. 161, Aug. 12, 2015, 15 pages.
Schaschke, "Dictionary of Chemical Engineering", Oxford University Press. Retrieved from hhttps://app.knovel.com/hotlink/pdf/id;kt00TW6WYC/dictionary-chemical-engineering/specific. At least as early as Dec. 31, 2014.
Office Action from corresponding Chinese Application No. 2021106864642, dated May 9, 2022.
Kazemi et al., "Evaluation of Different Vapor Recompression Distillation Configurations Based on Energy Requirements and Associated Costs," Applied Thermal Engineering, vol. 94, 2016, pp. 305-313.
Chinese Office Action in corresponding Chinese Patent Application No. 2021106864642, dated Oct. 26, 2022.

* cited by examiner

SYSTEM FOR SEPARATING GAS

FIELD OF THE DISCLOSURE

The disclosure relates to an improved system for separating gases from a stream, in particular for removing $CO_2$ from a methanol synthesis product stream. The system may comprise a stripper portion for removing $CO_2$ from an overhead stream of a distillation column. The system may further comprise a split tower design for the distillation column with an integrated vapo-condenser and may utilize mechanical vapor recompression.

BACKGROUND

Global climate change has been deemed to be the "most pressing environmental challenge of our time." The National Aeronautics and Space Administration (NASA) cites that "scientific evidence for warming of the climate system is unequivocal." Climate change results from the warming effects of greenhouse gases such as water vapor, nitrous oxide, methane, and carbon dioxide. Of these, carbon dioxide emissions are a key culprit, as global atmospheric concentration of $CO_2$ has increased by a third since the Industrial Revolution began. $CO_2$ emissions largely stem from human activities, such as the consumption of fossil fuels, the byproducts of which are emitted into the atmosphere.

One of the ways that nations have attempted to address climate change is by discussing and implementing carbon cap-and-trade policies, which cap total carbon emissions and allow companies to trade for allowances to create emissions. Such policies create strong needs for net carbon emitters such as utility and chemical companies to reduce carbon emissions for both the purpose of trading credits to other net carbon emitters and to avoid paying for additional allowances.

In further response to climate change concerns, solar and wind energy production has increased significantly in recent years, but still suffers from a number of fundamental engineering limitations: most solar and wind energy is primarily available and is therefore produced in areas far removed from population and industrial areas that consume the power; for example, most wind power potential in the U.S. is in the Great Plains region, and most solar power potential is in the southwest, whereas population centers are largely concentrated along the coasts. The result of renewable electricity being produced in these remote locations is high costs and substantial loss of power as the solar and wind power is transmitted over long distances. Additionally, most of the energy delivered to consumers is not in the form of electricity, but rather in the form of transportation fuel, heating gases, or otherwise. Only a small percentage of transportation energy is provided by renewable electricity.

Renewable electricity also cannot be stored in industrially significant quantities or at economically feasible costs, which leads to much of solar and wind electricity being wasted or grounded during times when solar and wind production is high but grid capacity is already maxed out, or when demand for electricity is low. As such, solar and wind power are normally underwritten by fossil-fuel sources, such as coal and natural gas power plants, which may provide baseline or backup power when solar and wind power are not sufficient to meet demand. There is therefore a need for a renewable form of energy that overcomes the deficiencies of renewable electricity to meet energy demands by storing energy and facilitating more efficient transportation of the energy to markets.

Converting $CO_2$ into methanol, which is a vital precursor for transportation fuels, industrial chemicals such as formaldehyde, as well as plastics, paints, textiles, and other dispositions, is an effective alternative disposition for $CO_2$, and an improved method for storing energy such as from renewable sources as methanol can store the renewable energy in its chemical bonds and overcomes numerous transportation-related problems of renewable electricity. For instance, the favorable energy density and liquid state of methanol, its compatibility with transportation fuels, and lower losses during transportation render methanol an advantaged energy-storage medium.

Further, given the massive global scale of methanol demand—200,000 tons per day and growing—diverting $CO_2$ from the atmosphere and into methanol has the potential to recycle a large quantity of the greenhouse gases responsible for climate change. Methanol also has significant potential for growth as a transportation fuel. Another increasing disposition for methanol includes methanol-to-olefins processes that convert methanol into the building blocks of polyolefins, the most common plastic product for which there is an ever-growing global demand.

Methanol is typically produced in industrial settings from synthesis gas ("syngas"), a combination of varying amounts of $H_2$, CO, and $CO_2$ frequently derived from gasified coal. Processes for synthesizing methanol from syngas typically entrain CO and $CO_2$ coproducts along with the methanol product. These coproducts must be separated from the methanol product prior to the final disposition of the product.

Typical processes for removing gases such as CO and $CO_2$ involve a dedicated light-ends separation process, which usually entails separate and capital-intensive fractionation column(s) and associated separations equipment as well as energy consumption in addition to the primary distillation column. Energy is consumed in both a reboiler and a condenser for said fractionation operation. The light-ends fractionation process is necessary because of the high solubility of $CO_2$ in methanol which cannot therefore be adequately separated by a simple flash operation. The separation of entrained CO and $CO_2$ byproducts from the desired methanol product is, as a result, highly expensive and inefficient.

Reactors used in methanol synthesis from syngas are typically limited to boiling water reactors due to the high heat profile of typical reaction suites, which include substantial amounts of CO. BWRs are complex and expensive equipment but are typically necessary in order to mitigate the heat generated from the exothermic production of methanol from syngas in order to protect the reaction product, the reactor, and the catalyst.

Other processes for separating gases such as CO and $CO_2$ from a product stream may involve flash separation prior to distillation, but this is not sufficient or desirable because of its inherently incomplete one-stage equilibrium separation, which sacrifices product to the waste gas stream and does not remove all of the dissolved coproducts.

Other separation processes include membrane separation and solvent separation (such as amine scrubbing), but these processes are costly, inefficient, and ill-suited to methanol production. Consequently, distillation remains the primary method for purifying many chemical products and is one of the most extensively used operations in chemical process industries.

Column distillation or fractionation is a highly energy-intensive operation (as distillation uses heat as the separating medium), accounting for 40-60% of the energy used by the chemical process industry, equivalent to at least 1.2 million barrels of crude oil per day. Distillation alone accounts for 6% of total U.S. energy use and 3% of global energy use. The massive energy consumption of distillation operations is at least partly due to the inefficiency of existing distillation processes (5%-10% is normal). An improved separations process therefore has potential to reduce energy-related emissions significantly.

From the foregoing, there is a need for an improved system for separating gases, in particular $CO_2$, from a product stream, in particular a methanol product.

SUMMARY

The problem of distillation processes, including in renewable transportation fuel contexts, being energy- and emissions-intensive, is addressed by embodiments of the system for separating gas of the disclosure. An entire distillation stage may be omitted, and associated energy expenditure and emissions avoided, by providing an advantaged reaction suite that generates fewer light-end byproducts and a separations section that removes light-end byproducts such as $CO_2$ with a stripping gas without the need for a dedicated light-ends distillation column.

The separations embodiments described herein are not limited to methanol purification processes, but may be used in any chemical process where improved systems and/or methods for the separation of gases from a process stream is required or desired.

An embodiment of the system for separation of gases preferably includes a reactor producing a crude product stream and a fractionation column connected at an overhead section to a heat exchanger such as a condenser and a stripper unit. A stripping fluid stream is flowed through the stripper unit to selectively remove impurities such as $CO_2$ from the overhead stream of the fractionation column after the overhead stream has been condensed in the heat exchanger. The reactor may advantageously utilize a reaction suite that primarily consumes $CO_2$ (rather than CO) as a feedstock for methanol synthesis, thereby providing a viable alternative disposition for $CO_2$ emissions as well as further simplifying the separations section, as described below.

The reaction suite may further produce a crude methanol product stream that comprises substantially only methanol, water, and $CO_2$. Existing reaction suites produce light end impurities that form azeotropic mixtures with methanol, such as acetone, ethyl formate, methyl acetate, and methyl propionate, with the primarily observed azeotropic impurity being acetone. Azeotropic mixtures are extremely difficult to separate, and often require special separations techniques and equipment such as pressure-swing distillation or addition of another chemical species.

Light-end impurities such as these are advantageously avoided by the reaction suite of embodiments of the disclosure, thus effective purification of the crude methanol product may be achieved by a single column-separation followed by a stripping operation, without the need for a dedicated light ends column to further separate the desired product from impurities in the condensed overhead stream, or a heavies column to remove heavy oil impurities, or other special separations techniques. This arrangement reduces required fractionation duties, operational complexities, and associated capital costs.

In variations of the system for separating a gas, the stripper unit is a gas-sparger unit integrated with a reflux drum, the reflux drum being configured to receive the condensed overhead stream from the heat exchanger. The gas-sparger unit flows or conducts a stripping fluid, such as $N_2$ or $H_2$ gas, through the condensed overhead stream in the reflux drum to selectively remove $CO_2$ from the methanol product without the use of a dedicated separation column to remove $CO_2$.

The crude methanol composition and stripper unit advantageously allow for flexible operation, as numerous advantageous stripping fluids may be used, including $H_2$, $N_2$ gas, water vapor, natural gas, $O_2$, noble gases, deuterium, etc. The system may thus be adjusted to the specific configuration of products and reactants needed and available in numerous industrial contexts. For instance, the system may be flexible to allow the use and production of deuterium to create deuterated methanol, with heavy water byproduct separated during distillation and light-end byproducts separated from the methanol product through the stripper unit of embodiments of the disclosure.

Existing attempts to utilize stripping technologies to separate gases such as $CO_2$ from methanol product streams are limited by process configurations and sources of stripping fluids to pre-distillation stripping. For example, EP 2 831 025 to Akzo Nobel N.V. of Amsterdam, Netherlands discusses the use of $H_2$ gas to strip certain species out of a methanol product stream. Noting that wet $H_2$ sources—$H_2$ obtained from aqueous electrolysis processes, particularly production of chlorine or sodium chlorate—are a more affordable source of $H_2$ than dry $H_2$ sources (due at least in part to the absence of a dedicated drying step), the embodiments of EP 2 831 025 integrate the drying stages for wet $H_2$ with a pre-distillation stripping stage. This arrangement necessarily relies on the water that is mixed with the methanol product upstream of the distillation stage to condense/remove water from the wet $H_2$ stripping fluid, as the $H_2$ stripping fluid forms the fresh $H_2$ feedstock to the reactor. (EP 2 831 025 p. 4 ll. 26-34).

A person skilled in the art would not be motivated nor find it apparent to mount the stripping unit of EP 2 831 025 at the overhead portion of a distillation unit, as EP 2 831 025 is disadvantageously limited to $H_2$ stripping (as $H_2$ stripping fluid is also the fresh $H_2$ feed to the reactor, thereby precluding the operational flexibility of using different stripping fluids at different times, as is contemplated by the embodiments of the disclosure), and is limited to drying a wet-$H_2$ source through the water in the pre-distillation product stream. The use of the wet $H_2$ of EP 2 831 025 to strip the overhead portion of a distillation column would contaminate the overhead product of the distillation with condensed water, defeating the purpose of the separation entirely and rendering the product methanol less valuable.

In another embodiment of the system for separation of gases, a separations process for purifying the methanol product makes use of a split-tower arrangement. The bottom section of the split column may operate at a higher pressure than the top section of the split column. The higher operating pressure of the bottom section of the split column prevents decomposition of the methanol product. The reflux of the bottom section of the split column may be integrated with the reboiler of the top section of the split column, utilizing a single heat-exchange device to reduce the total duties for the fractionation operation.

In variations of the split-column design, the reboiler of the top section of the column and the condenser of the bottom section of the split column are heat integrated in a single heat-exchange device, for example a vapo-condenser, owing to the pressure differences between the top and bottom sections of the split column. Total duty is minimized by utilizing the heat in the higher-pressure column to reboil the bottoms of the lower-pressure column while condensing the overhead stream from the higher-pressure column. By heat integrating the columns, the required duty to be added in the condenser at the overhead of the lower-pressure column and in the reboiler at the bottom of the higher-pressure column is reduced. The energy savings realized through this arrangement further contributes to emissions reductions.

In particular embodiments, the single heat-exchange device may optimize temperature approach (and as a result enhance thermodynamic efficiency) between the integrated reboiler and condenser streams and thus between the two columns by utilizing a falling-film evaporator or thermosiphon design. The improved (lower) temperature approach of falling-film evaporator- and thermosiphon-type heat exchangers (approximately 1-2° C.) compared to the temperature approach of kettle reboilers (approximately 10° C.) enables a lower operating pressure in the higher-pressure column, as the pressure required for the overhead stream to provide sufficient reboiler duty for the lower-pressure column is reduced. This minimizes capital and operating costs (because the required reboiler duty is reduced and the column itself may be reduced in size) and reduces overall energy consumption, which puts further downward pressure on emissions.

In variations of the split column process, the split column may utilize mechanical vapor recompression to further improve thermodynamic efficiency by taking a side cut from the top section of the column, recompressing the side cut, and then feeding the compressed side cut to the bottom section of the column.

This advantageously improves the efficiency of the separation by substituting the increased temperature and pressure resulting from recompressing the side cut for the duty that would otherwise be required of a dedicated reboiler for the bottom section of the column. This arrangement thereby further reduces capital costs and operating costs.

The overhead condenser may be provided as two condensers in a parallel or series relationship, with a first condenser condensing a first portion of an overhead stream of a fractionation column, and uncondensed gases from the first condenser being condensed in the second condenser, maximizing the methanol capture without entraining unwanted $CO_2$ gases back into the liquid methanol product.

Other methods, embodiments, and variations of the system for separating gases are described in greater detail in the following discussion.

BRIEF DESCRIPTION OF THE DRAWINGS

These and other features, aspects, and advantages of the present invention will become readily apparent and better understood in view of the following description, appended claims, and accompanying drawings.

DETAILED DESCRIPTION OF VARIOUS EMBODIMENTS

A better understanding of different embodiments of the disclosure may be had from the following description read with the accompanying drawings in which like reference characters refer to like elements.

While the disclosure is susceptible to various modifications and alternative constructions, certain illustrative embodiments are shown in the drawings and will be described below. It should be understood, however, there is no intention to limit the disclosure to the embodiments disclosed, but on the contrary, the intention is to cover all modifications, alternative constructions, combinations, and equivalents falling within the spirit and scope of the disclosure and defined by the appended claims.

It will be understood that, unless a term is defined in this patent to possess a described meaning, there is no intent to limit the meaning of such term, either expressly or indirectly, beyond its plain or ordinary meaning.

The term "stripper unit" as used in this disclosure has its ordinary meaning and denotes any unit suitable for selectively stripping or driving a species, preferably a gas, out of another fluid.

The terms "separation column" or "fractionation column" as used in this disclosure have their ordinary meaning and denote any column configuration suitable for distilling or separating two or more components, including tray columns, packed columns, binary columns, multi-component columns, split feed columns, or otherwise.

Reaction Suite

Existing methanol synthesis reactions utilize syngas as a feedstock, typically comprising primarily CO, using $H_2$ to produce methanol using primarily the following reaction: $CO+2H_2 \rightleftharpoons CH_3OH$. However, this reaction yields numerous byproducts that are undesirable in various methanol dispositions and in that they make separation of methanol expensive and difficult, both in terms of required equipment and energy costs. There is a need for a reaction suite that minimizes impurities so as to allow for a simpler and more cost-effective separations process.

Figure 1:
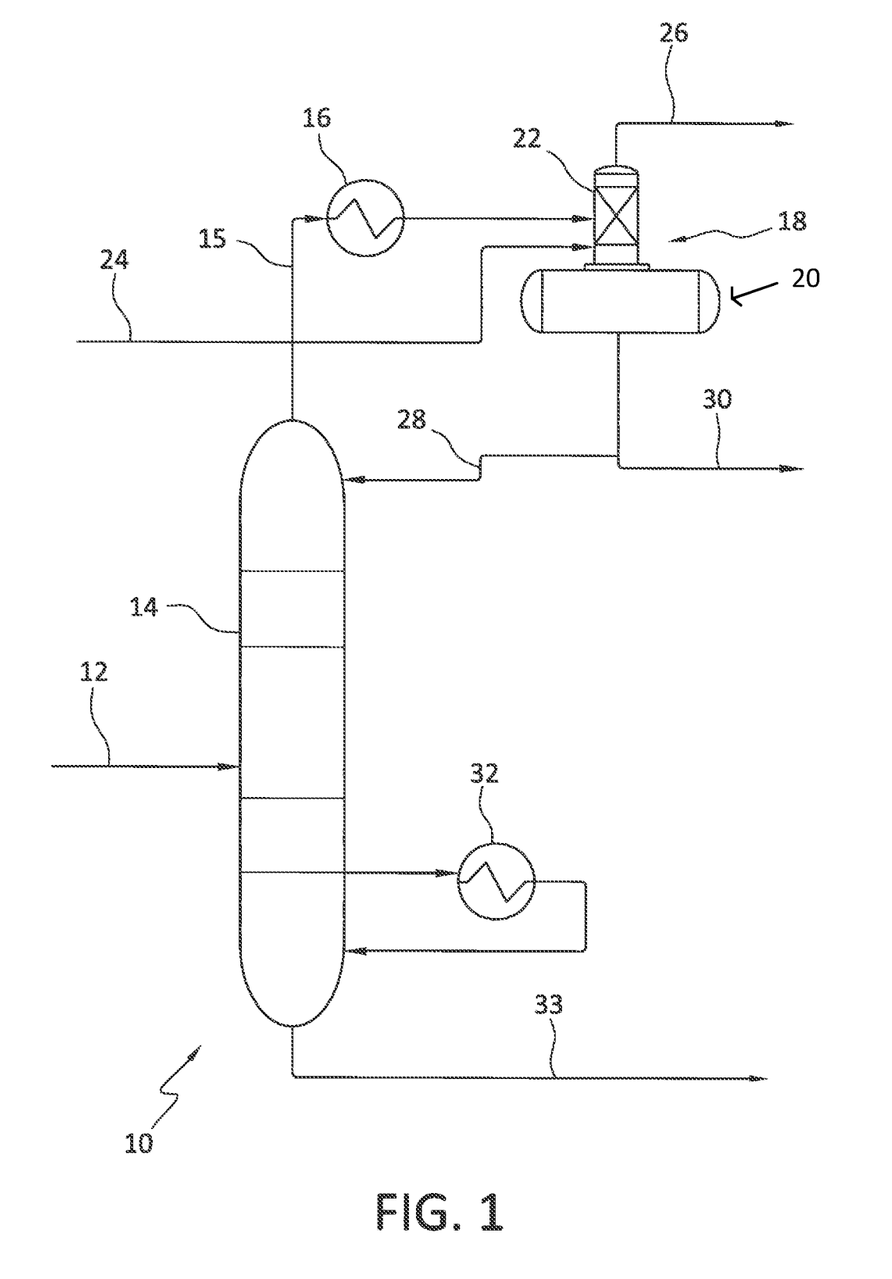
FIG. 1 is a simplified diagram of a separations system according to the disclosure.

FIG. 1 shows a separating system 10 according to an embodiment of the disclosure. A crude methanol stream 12 is directed from a reaction section to a fractionation column 14. Crude methanol stream 12 comprises substantially only methanol product, water, and $CO_2$. This composition, which is advantageously free of light end contaminants and heavy contaminants, may be accomplished by synthesizing methanol via a catalyst selection and a reaction suite that uses $CO_2$ as a starting material rather than CO (such as is used by existing methanol facilities). In particular, the chemistry is reduced to the following two reactions:

(Reaction 1)

(Reaction 2)

By using Reactions 1 and 2 to synthesize methanol, crude methanol stream 12 comprises substantially only methanol, water, and $CO_2$, simplifying the separations process as CO byproduct and undesirable light end contaminants such as acetone, ethyl formate, methyl acetate, and methyl propionate (with the primarily observed azeotropic impurity being acetone), are avoided and thus need not be separated. These light end contaminants are known to create azeotropic mixtures with methanol, separations of which are extremely difficult and costly, as such mixtures may require using pressure-swing distillation and/or adding a third chemical species to separate.

Heavy contaminants, such as heavy oils, are also largely avoided by the use of Reactions 1 and 2, simplifying the separation of bottoms products such as $H_2O$. The use of Reactions 1 and 2 further uses $CO_2$ as a starting material to provide an alternative disposition for $CO_2$ emissions, and facilitates a simpler and more efficient separations process, as will be described herein.

In an embodiment, and as will be discussed in greater detail hereafter, Reactions 1 and 2 may take place in a modified reactor. Reactions 1 and 2 advantageously have a less intense exotherm than existing reaction suites for methanol synthesis, enabling the use of tube-cooled reactors as the primary reactor. The use of a tube-cooled reactor is advantageous over existing reactor configurations, primarily boiling water reactors which are required to deal with large exotherms associated with existing reaction pathways, in terms of the lower cost, higher efficiency, and relative simplicity of operation of tube-cooled reactors. Additionally, tube-cooled reactors are preferred as being more efficient than adiabatic or cold-shot reactors which are inefficient and require multiple reactors in series to achieve desired conversion rates. Further, improving the heat distribution with the reactor helps to prevent catalyst sintering, thereby extending the life of the catalyst and minimizes process interruptions.

Utilizing Reactions 1 and 2 further enables the production of methanol to be coupled with GHG-producing processes to recycle $CO_2$ rather than emitting $CO_2$ to atmosphere. For example, the system for separating gases of the disclosure may be provided at a power plant, oil refinery, chemical plant, mine, manufacturing facility, agricultural facility, heating unit, processing plant, or any other facility, entity, or location that emits $CO_2$. The system may be arranged as a standalone unit, an integrated unit, or as a bolt-on unit.

Gas Stripper

Because all distillation processes require energy input, often through the reboiler and condenser, to achieve separation of the components, and therefore produce emissions, there is a need for a separations section that minimizes the number of distillation operations required to achieve desired separation of the components, and consequently minimizes equipment and operating costs, as well as emissions. Existing methanol synthesis operations typically comprise a column that is dedicated to separating light components (meaning components having a lower boiling point than the methanol product such as CO, $CO_2$, etc.), and consequently generate emissions. There is a need for a process that eliminates the need for a dedicated column with its associated emissions to separate components.

In an embodiment of the disclosure depicted in FIG. 1, reactor effluent contained in crude methanol stream 12 is fed to separations section 10 which comprises fractionation column 14 and accompanying equipment. Owing to the composition of the crude methanol stream 12 which contains methanol, water, and virtually no CO or other light contaminants besides $CO_2$, only a single fractionation column 14 is required for purifying the desired methanol product. This is a singular advantage over most methanol purification processes which comprise dedicated light ends columns and associated equipment such as reboilers, condensers, drums, etc. in order to achieve adequate purification of the product. A condenser 16 and a reboiler 32 provide the required duty for the fractionation column 14 to separate the crude methanol stream 12 into on-spec products. The fractionation column 14 may comprise a stripping section, a rectifying section, and a feed section.

An overhead stream 15 of the fractionation column 14 comprises both methanol and $CO_2$, as the water is less volatile and therefore is collected and sent to battery limits or other processes via a bottom stream 33. The overhead stream 15 is condensed in a condenser 16 and then stripped of $CO_2$ in an integrated stripper/reflux drum 18. Integrated stripper/reflux drum 18 comprises a stripper portion 22 which is connected to a reflux drum 20. The integrated stripper/reflux drum 18 advantageously removes dissolved $CO_2$ from the methanol product without the use of heat or a separate, dedicated fractionation column, reducing energy requirements and therefore emissions.

The integrated stripper/reflux drum 18 drives the $CO_2$ out of the methanol in the condensed overhead stream by introduction of a stripping or carrier gas such as $H_2$, $N_2$, or other suitable gas. Other suitable gas species may include natural gas, noble gases, $O_2$, water vapor, deuterium, etc., depending on process requirements and facility considerations. For example, $N_2$ may be abundantly available in certain chemical plants with which the system for separating gases is associated and may recommend itself as a suitable stripping gas. In certain petrochemical or refining facilities, $H_2$ may be more abundantly available and therefore may be suitable as a stripping gas. Other facilities, infrastructure constraints, and economic considerations may recommend other gaseous species as stripping gases.

In an embodiment of the system, the stripper portion 22 is a gas sparger which is integrated with the reflux drum 20. The gas sparger 22 introduces the carrier gas from the stream 24 into the condensed overhead stream 15 collected within the reflux drum 20, the carrier gas contacting and entraining the dissolved $CO_2$, thereby stripping the $CO_2$ out of liquid methanol in the reflux drum 20. The gas sparger 22 may, in an embodiment, introduce the carrier gas by bubbling the carrier gas up through the collected liquid within the reflux drum portion 20 of the integrated stripper/reflux drum 18. The combined carrier gas and $CO_2$ are ejected from the integrated stripper/reflux drum 18 in the form of a waste gas stream 26 that may be disposed of in various ways; for example, the waste gas stream 26 may be scrubbed of entrained methanol in a scrubber unit prior to being released to the atmosphere or being recycled/reprocessed as additional feedstock to the reactor. Alternatively, the waste gas stream 26 may be fed directly back into the loop as additional feedstock or disposed directly to battery limits or another process.

The remaining liquid methanol in the reflux drum 20 is split between a reflux stream 28 which is directed back to the fractionation column 14 to facilitate the distillation of methanol and $CO_2$ from water and other heavy components, and a methanol product 30 which may be directed to battery limits, storage, or other disposition. Thus by utilizing Reactions 1 and 2 to produce a crude methanol stream comprising substantially only methanol, $CO_2$, and water, and by driving off the dissolved $CO_2$ from the overhead stream 15 of a single fractionation column 14 without the use of added heat by introducing a carrier gas in a stripper unit 22, on-spec methanol product 30 may be obtained without the use of a dedicated light-ends column, with its attending capital and energy expenditures.

Figure 2:
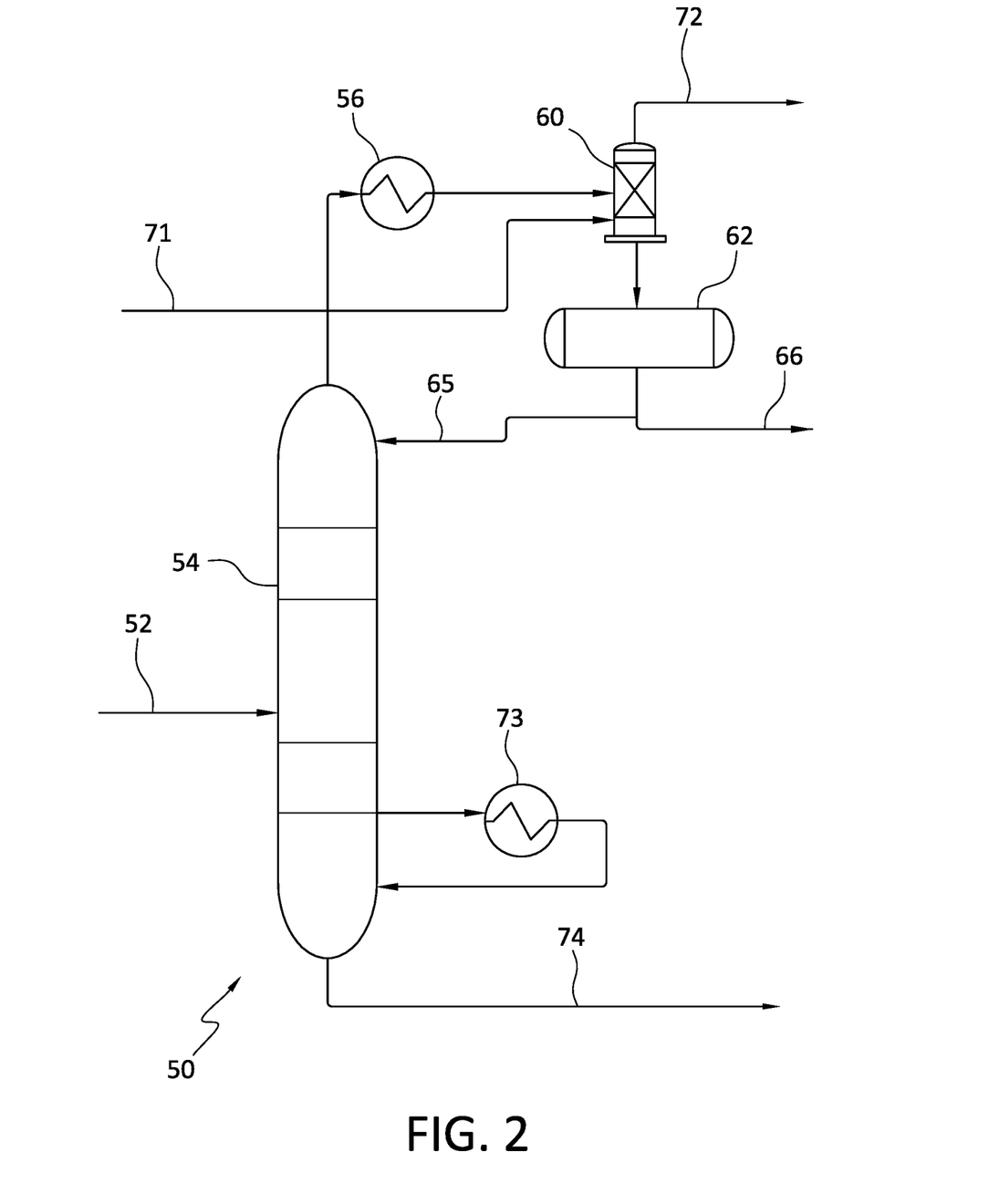
FIG. 2 is a simplified diagram of an embodiment of the separations system of FIG. 1.

In an alternative embodiment depicted in FIG. 2, a crude methanol stream 52 which similarly comprises substantially only methanol, water, and $CO_2$ is fed to a separations section 50 which comprises a single fractionation column 54. A condenser 56 and a reboiler 73 provide required duty for the fractionation column 54 to separate crude methanol stream 52 into on-spec products, including a methanol product 66 and a waste water product 74. The overhead stream from the fractionation column 54 is condensed in the condenser 56 and fed to a stripper unit 60. Unlike the embodiment of FIG. 1, the stripper unit 60 is not integrated or integrally formed with the reflux drum 62. A carrier gas is fed to the stripper unit 60 via stream 71, and waste gas stream 72 comprises combined carrier gas and $CO_2$ which has been removed from the methanol product in the stripper unit 60. As with the waste gas stream 26 of FIG. 1, the waste gas stream 72 may be disposed of such as by being scrubbed of entrained methanol prior to atmospheric release or may be recycled/reprocessed as additional feedstock to the reactor.

Stripped liquid methanol is fed from the stripper unit 60 to the reflux drum 62, and is then split into a methanol product stream 66 which may be disposed toward battery limits, storage, or other processes, and a reflux stream 65, which is returned to the fractionation column 54 as reflux to facilitate the distillation of methanol and $CO_2$ from water and any other heavy contaminants.

The embodiment depicted in FIG. 2 demonstrates that the stripper unit 60 need not be integrally formed with the reflux drum 62 but rather may be separately arranged, as determined by the process requirements of a specific configuration or facility. For example, in a retrofit operation, a stripper unit may be provided to cooperate with an existing drum of an existing distillation column, or vice versa.

Figure 3:
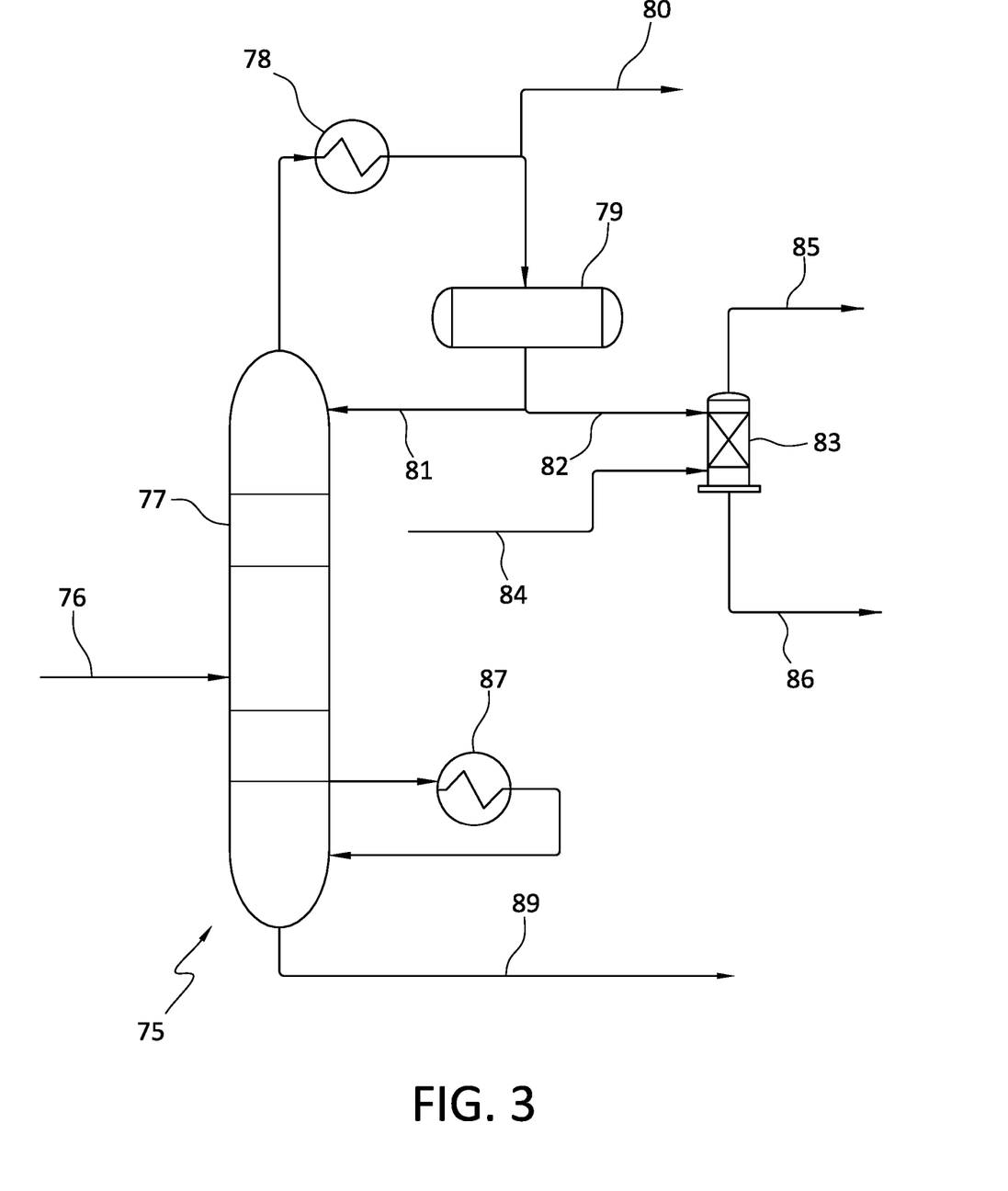
FIG. 3 is a simplified diagram of an alternative embodiment of a separations system according to the disclosure.

In an alternative embodiment depicted in FIG. 3, a crude methanol stream 76, which comprises substantially only methanol, water, and $CO_2$, is fed to a separations section 75 which comprises a single fractionation column 77 and associated equipment. A condenser 78 and a reboiler 87 provide the required duty for the fractionation column 77 to separate crude methanol stream 76 into on-spec products, including a methanol product 86 and a waste water product 89. An overhead stream from the fractionation column 77 is condensed in the condenser 78.

In the embodiment of FIG. 3, the condensed overhead stream is split into two streams. A stream 80 contains a first fraction of $CO_2$ as well as entrained methanol and may be removed from the process as it comprises mainly gas, thanks to a condenser 78 facilitating a rough separation of gaseous $CO_2$ (containing entrained methanol) and liquid methanol (containing dissolved $CO_2$). As with waste gas streams 26 and 72 in the aforementioned embodiments depicted in FIGS. 1 and 2, the stream 80 may be scrubbed of entrained methanol prior to atmospheric release or may be recycled/reprocessed as additional feedstock to the reactor. The scrubbed methanol may be returned to the process as reflux, added to the methanol product stream, or otherwise disposed to another process or to battery limits.

A remaining portion of the condensed overhead stream containing primarily liquid methanol with dissolved $CO_2$ is sent to a reflux drum 79. After being collected in the reflux drum 79, the remaining portion of the condensed overhead stream may be split, with a portion or a stream 81 returning to the fractionation column 77 as reflux to facilitate the distillation, and a portion or stream 82 being sent to the stripper unit 83 for removal of dissolved $CO_2$. As with the stripper units 22 and 60 of the aforementioned embodiments, the stripper unit 83 drives dissolved $CO_2$ out of the liquid methanol through the introduction of a carrier gas such as $H_2$, $N_2$, or any other suitable species in a stream 84, as discussed previously.

The stripper unit 83 produces a waste gas stream 85 comprising the carrier gas, $CO_2$, and some amounts of entrained methanol. The waste gas stream 85 may be scrubbed of entrained methanol product prior to atmospheric release and/or recycled/reprocessed as additional feedstock to the reactor. Because the first fraction of $CO_2$ was removed from the process via stream 80, waste gas stream 85 contains less $CO_2$ than stream 80 and waste gas streams 26 and 72 of the aforementioned embodiments on both a mass flow basis and a mass fraction basis. As such, waste gas stream 85 may be suitable for different dispositions than waste gas streams 26 and 72 due to its lower $CO_2$ content. On-spec methanol product in stream 86 is obtained in this embodiment from a bottom portion of stripper unit 83.

The embodiment depicted in FIG. 3 demonstrates that the stripper unit 83 may be arranged either upstream or downstream of a reflux drum 79, as determined by the process requirements of a specific configuration or facility, and that certain gases may advantageously be separated upstream of a reflux drum, rendering the stripped gas viable for different dispositions.

A reboiler 87 provides duty necessary to reboil a bottom fraction of the crude methanol stream 76, vaporizing methanol product and $CO_2$ while collecting water and any other trace heavy species, such as long-chain alkanes, higher alcohols, higher ketones, and esters of lower alcohols with formic, acetic, and propionic acids. The fractionation column 77 removes a waste water stream from a bottom portion.

By providing the aforementioned embodiments, the problem of separations processes, in particular crude methanol purification, requiring a dedicated light-ends fractionation column with its associated emissions to remove gaseous species, such as $CO_2$, is advantageously solved.

Split Tower Arrangement

Distillation is a highly energy-intensive process because of the inherent inefficiency of the separation process, which requires large duties in both the reboiler and condenser, as well as significant reflux rates to achieve desired separation. This leads to high operating and capital costs. In facilities or processes where substantial heat is left over from initial reaction units (due to reaction or thermal inefficiencies, or high reaction exotherms) or from associated processes at the same facility or site as the separation process, the leftover heat often being in the form of generated steam, waste heat may be used to provide duty to the reboiler of certain distillation operations.

However, such an arrangement may be undesirable in the first instance, as the generation of substantial waste heat in the reaction phase or in associated processes represents a thermodynamic inefficiency and consequently a negative effect on emissions from the facility. It is therefore desirable to minimize the generation of waste heat as much as possible as opposed to trying to salvage the waste heat. Accordingly, it is also desirable to minimize heat requirements of processes located downstream of the reaction process which may otherwise utilize waste heat, such as in reboilers. By so doing, requirements for added heat may be reduced. There is a need for an improved separations process which enhances thermodynamic efficiency in order to minimize heat requirements and consequently energy expenditures and emissions.

Figure 4:
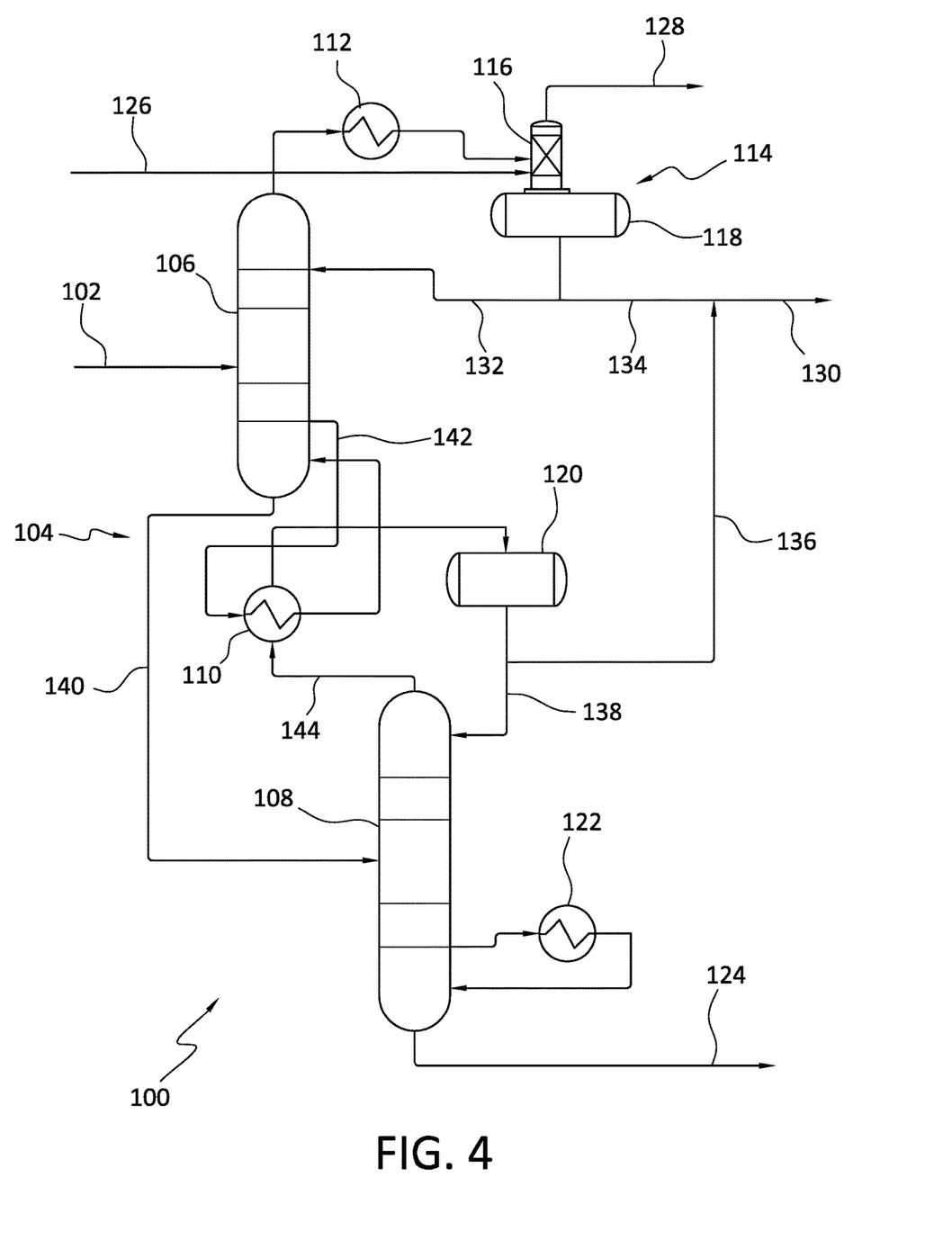
FIG. 4 is a simplified diagram of an alternative embodiment of a separations system according to the disclosure.

In an alternative embodiment of a system for separating gases depicted in FIG. 4, a crude methanol stream 102 is fed to a separations section 100, which comprises a fractionation column 104. The fractionation column 104 is arranged in a split-tower arrangement comprising a top or low-pressure (LP) section 106 and a bottom or medium-pressure (MP) section 108. The LP section 106 and the MP section 108 are connected by stream 140 which comprises primarily methanol and water, as well as by heat integration between the condenser of the MP section 108 and the reboiler of the LP section 106. A vapo-condenser 110 integrates the functions of both condensing an overhead stream 144 of the MP section 108 and reboiling a bottom stream 142 of the LP section 106. The operating pressure of the MP section 108 is calibrated to be sufficiently high such that the condensation of a stream 144 provides the required duty to reboil a stream 142.

The use of the split-tower arrangement of the separations section 100 enhances thermodynamic efficiency by reducing the total duty required in the fractionation column 104, as the duties that are integrated in the vapo-condenser 110 would otherwise be provided in a condenser at the overhead of the MP section 108 and a reboiler at the bottom of the LP section 106, or in increased duties to the LP section 106 condenser and the MP section 108 reboiler.

As in certain previous embodiments, an overhead stream comprising substantially only $CO_2$ and methanol from LP section 106 is fed to a condenser 112 and then to an integrated stripper/reflux drum 114 which comprises a stripper section 116 and a reflux drum 118. The stripper section 116 and reflux drum 118 may, in alternative embodiments, be distinct units, such as is shown in the embodiment depicted in FIG. 2, as required by process configurations and/or facility requirements. $CO_2$ is removed from the condensed methanol by introduction of a carrier gas, provided through a stream 126. In certain embodiments, the stripper section 116 is a gas sparger. The gas sparger 116 introduces the carrier gas from the stream 126 into the condensed overhead stream in reflux drum 118 to drive the dissolved $CO_2$ out of solution with the liquid methanol and into a waste gas stream 128, which comprises substantially only $CO_2$ and carrier gas. The carrier gas may be $N_2$, $H_2$, or any other suitable and/or inert gas, such as water vapor, natural gas, noble gases, $O_2$, deuterium, etc., as required by specific process needs and product requirements. As with previous embodiments, the waste gas stream 128 may be scrubbed of entrained methanol prior to atmospheric release or being recycled/reprocessed as additional feedstock to the reactor.

The liquid methanol from reflux drum 118 is split into a reflux stream 132 which is returned to the LP section 106 to facilitate the distillation of methanol and $CO_2$ from water, and the LP section methanol product stream 134 which may be disposed similar to previous embodiments.

The MP section 108 separates the contents of a stream 140 into product methanol and waste water. Substantially no $CO_2$ is entrained in stream 140 because the $CO_2$ contained in the crude methanol stream 102 is isolated in the overhead stream of the LP section 106. A reboiler 122 provides duty at a bottom portion of the MP section 108. A waste water product is obtained at the bottom of the MP section 108 and is disposed of via a stream 124. A reflux drum 120 receives the condensed overhead stream of the MP section 108 and splits the condensed overhead stream into a reflux stream 138 which is returned to the MP section 108, and a MP section methanol product stream 136 which is combined with the LP section methanol product stream 134. A combined methanol product stream 130 can be sent to battery limits, storage, or to another disposition. In this embodiment, the MP section 108 does not comprise a stripper unit because substantially no $CO_2$ is entrained in the stream 140 and on-spec methanol product is obtained in the stream 136 without a dedicated unit to remove $CO_2$.

In alternative embodiments of the disclosure, a second stripper unit may be connected to the MP section reflux drum 120 in the same manner as a stripper section 116 is attached at the LP section reflux drum 118. A split stream from a stream 126 or a separate stream introduces carrier gas to the second stripper unit connected to the MP section reflux drum 120, and a waste stream comprising carrier gas and any $CO_2$ that is removed from the condensed overhead stream from the MP section 108 joins with a waste gas stream 128 to battery limits, scrubbing, or recycle. This embodiment may be employed, for example, to ensure that any trace $CO_2$ that is potentially entrained into MP section 108 is eliminated from the MP section methanol product. This may be desired in configurations producing methanol of exceptionally high purity.

In particular, this embodiment may be advantageous if, for example, the stream 140 comprises a sidecut stream rather than a bottom stream, or if the crude methanol stream 102 is fed to the MP section 108 rather than to the LP section 106. The second stripper unit may be integrally connected to the reflux drum 120, or may be separate, as in the embodiment depicted in FIG. 2. Additionally, in certain embodiments it may be advantageous to feed the crude methanol stream 102 to the fractionation column 104 at a location at the MP section 108, in which case a second stripper unit on the MP section 108 is desirable.

In yet further embodiments of the disclosure, the stripper section 116 may be distinct from the LP section reflux drum 118, as in the embodiment depicted in FIG. 2.

By providing the features of the depicted embodiment, the problem of separations processes requiring large amounts of energy and consequently generating unnecessary emissions, is advantageously addressed as the split-tower arrangement reduces required duties by integrating the reboiler and condenser of the LP section 106 and MP section 108, respectively in a single device.

Mechanical Vapor Recompression or Heat-Pump Distillation

In certain applications, available heat and/or steam (which is normally used to provide reboiler duty) is limited; for example, certain processes may not have a high exotherm and thus do not produce significant amounts of waste heat for steam generation which can be used to provide heat to other processes. In such applications, and in distillation generally, a separations section which minimizes heat requirements, such as in reboilers, is desirable to avoid the costs, both capital and operational, associated with steam generation to make up for heat recovered from hot sections of the process. Additionally, it is desirable to minimize capital costs by reducing the size and number of units required to carry out a separation operation.

Figure 5:
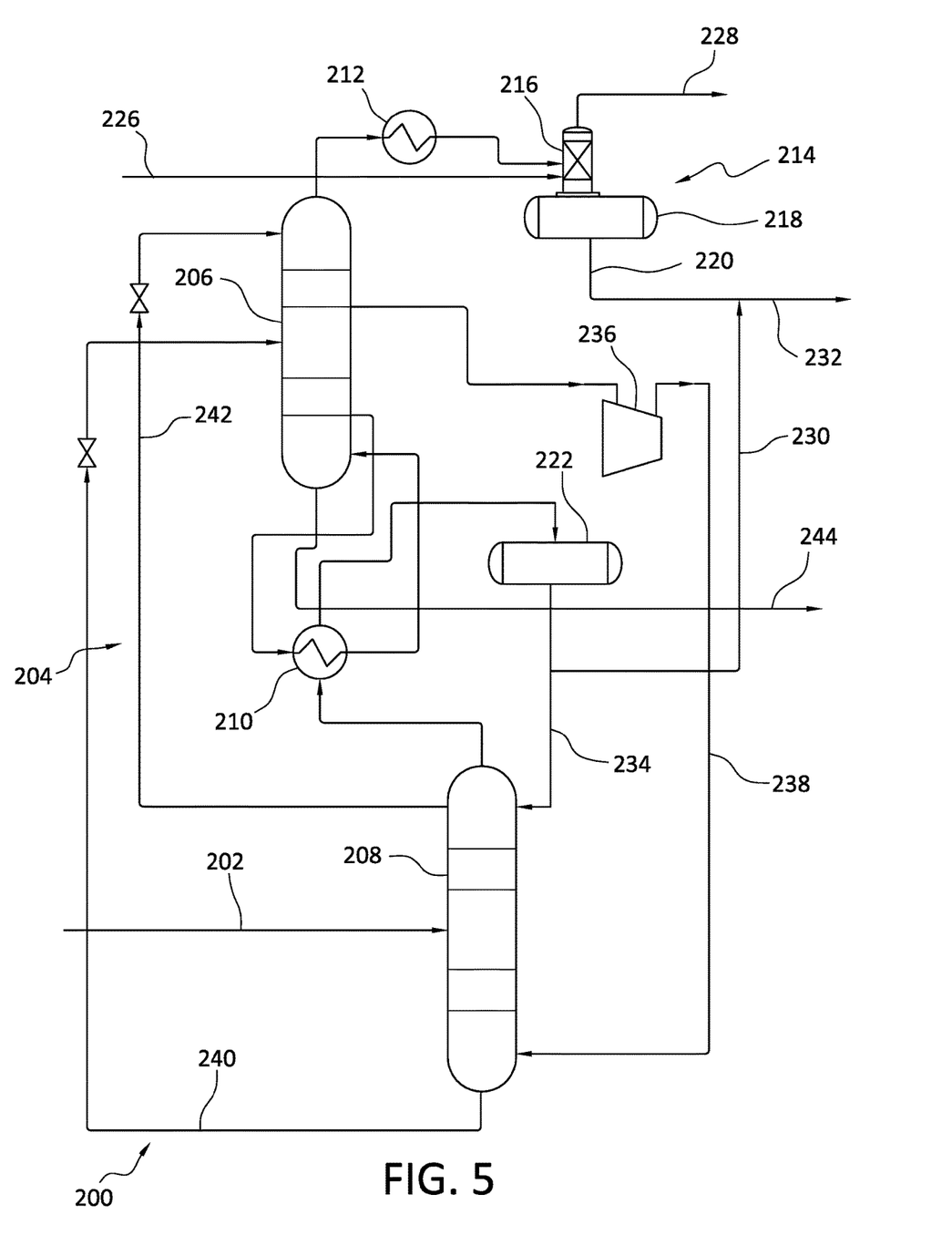
FIG. 5 is a simplified diagram of an alternative embodiment of the separations system of FIG. 4.

In another embodiment of the disclosure depicted in FIG. 5, a separations section 200 utilizes mechanical vapor recompression to further enhance the thermodynamic efficiency of the separation process. A crude methanol stream 202 containing substantially only methanol, water, and $CO_2$ is fed to a fractionation column 204, which is arranged in a split-tower arrangement similar to the embodiment of FIG. 4. A top or LP section 206 is heat integrated with a bottom or MP section 208 at a vapo-condenser 210 which condenses an overhead stream of the MP section 208 and reboils a bottom stream of the LP section 206, enhancing overall efficiency. A crude methanol stream 202 is received at an optimal location in the MP section 208. In alternative embodiments, the crude methanol stream 202 may be received at an optimal location in the LP section 206.

The LP section 206 and the MP section 208 are further connected by streams 240 and 242, which function to provide material balance and especially, in the case of a stream 242, to provide reflux for the LP section 206, thereby eliminating the need for a separate reflux stream from an overhead stream of the LP section 206. A waste water product is removed from the bottom of the LP section 206 in a stream 244.

As with previous embodiments, a condenser 212 condenses an overhead stream of the LP section 206 and feeds the condensed overhead stream to an integrated stripper/reflux drum 214. An integrated stripper/reflux drum 214 comprises a stripper unit 216 and a drum 218, the stripper unit 216 configured to selectively remove $CO_2$ from the methanol product by introducing a carrier gas from stream 226. As in previous embodiments, the stripper unit 216 and drum 218 may alternatively be distinct units (as shown in the embodiment of FIG. 2), and stripper unit 216 may be downstream of the drum 218, as in the embodiment of FIG. 3. In yet further embodiments, the stripper unit 216 may be a gas sparger, as in the embodiment depicted in FIG. 1.

$CO_2$ and carrier gas from the integrated stripper/reflux drum 214 are disposed of in waste gas stream 228, which may be scrubbed of entrained methanol prior to atmospheric release and/or recycled/reprocessed as additional feedstock for the reactor. The remaining liquid in the reflux drum 218 is fed via a stream 220 to be combined with methanol product from the MP section 208 to deliver an on-spec methanol product 232. Because the stream 242 provides reflux from the MP section 208, no reflux stream needs to be returned to the LP section 206 from the LP section 206 overhead stream. As a result, the required flowrate of the LP section 206 overhead stream is reduced and the required size of a condenser 212, as well as duty removed therethrough via cooling water, is consequently reduced. This advantageously reduces capital and operating costs, as well as emissions. In certain such embodiments, the drum 218 may be omitted.

An overhead stream from the MP section 208 is condensed in a vapo-condenser 210 and collected in a drum 222. From the drum 222, a reflux stream 234 may be directed to the MP section 208, and a methanol product stream 230 may be joined to the methanol product stream 220.

A sidecut from the LP section 206 is fed to a mechanical vapor recompression compressor (MVR compressor) 236 which compresses the sidecut to an operating pressure suitable for the MP section 208, thereby also raising the temperature of the sidecut. The recompressed sidecut 238 is fed to the MP section 208, preferably at a location near the bottom of the MP section 208. In this embodiment, the recompressed sidecut 238 replaces in its entirety the reboiler of the MP section 208, as the added enthalpy of the compressed sidecut serves to provide the necessary duty to reboil the MP section 208 and consequently the LP section 206. The addition of this duty by the MVR compressor 236 achieves enhanced thermodynamic efficiency and capital cost reductions compared to providing the duty through a reboiler unit.

Recompression of a stream may thus advantageously utilize compressor work to raise the pressure and consequently temperature of a portion of a process stream (such as a sidecut from a column 206) for the purposes of providing reboiler duty more efficiently than adding heat to the process through a conventional reboiler, especially a reboiler utilizing steam as a heat source and with fewer emissions. Recompressing an existing vapor stream to a higher temperature and pressure using a compressor advantageously bypasses the phase change inefficiencies inherent in steam generation from boiler feed water due to the high enthalpy difference between boiler feed water and pressurized steam. Mechanical vapor recompression therefore attains the desired increase in temperature and pressure with a much lower input of energy than traditional reboilers.

The efficiency of the mechanical vapor recompression is further enhanced by feeding the recompressed sidecut 238 directly to a bottom portion of the MP section 208 to replace the reboiler and the heat exchange inefficiencies associated therewith. The recompressed sidecut 238 can more efficiently transfer heat to the MP section 208 by interacting directly with the contents of the fractionation column 204. This arrangement reduces heating duties and capital costs by replacing the reboiler and its associated energy inputs with a recompressed process stream that adds heat directly to the contents of the MP section 208.

The use of mechanical vapor recompression thus addresses the problem of distillation and other process operations requiring added heat, which leads to increased emissions, by reducing heat requirements and capital costs through the use of mechanical vapor recompression of, for example, a sidecut stream.

Figure 6:
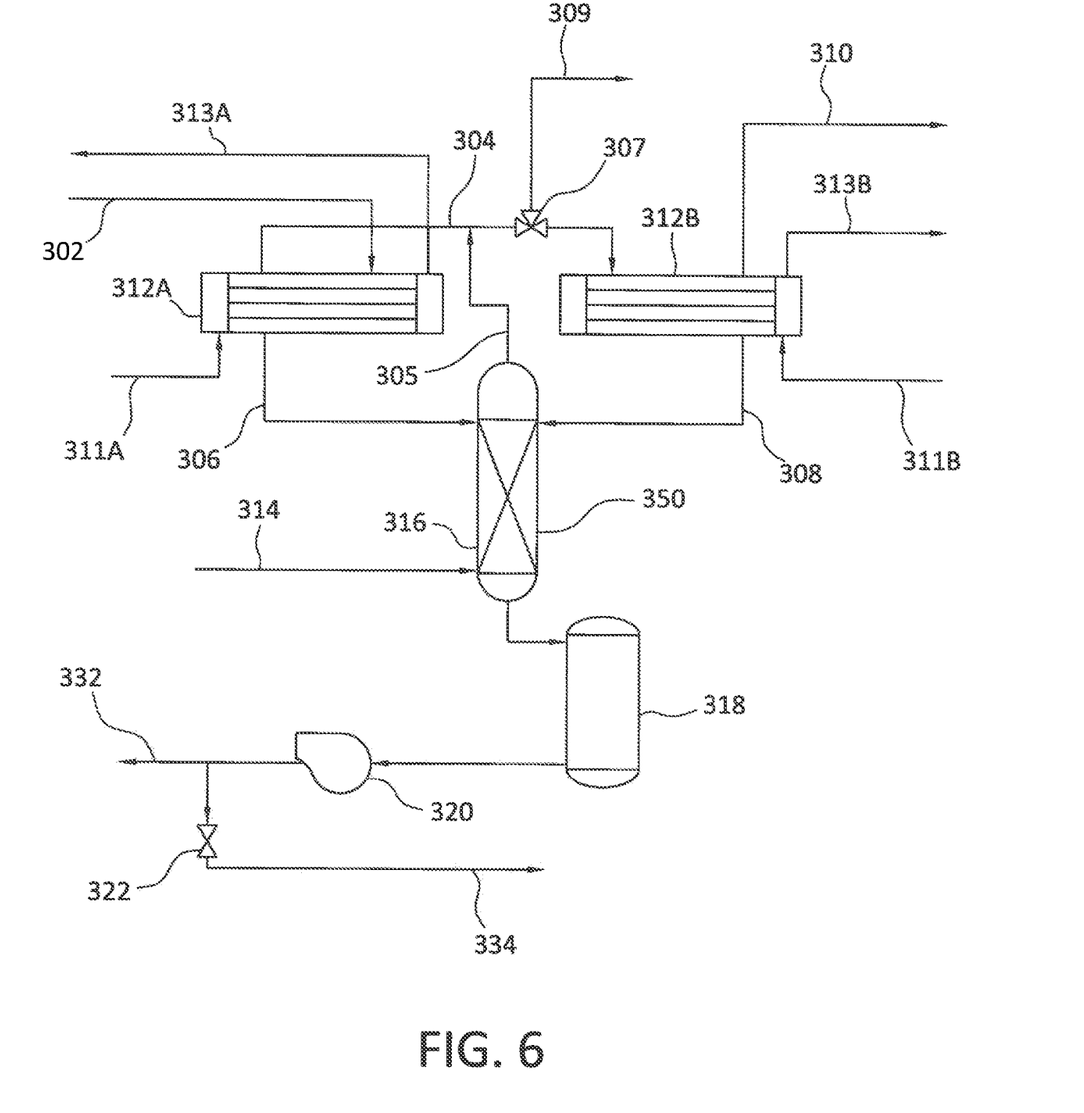
FIG. 6 is a simplified diagram of an alternative embodiment of a system for separating gases according to the disclosure.

In an alternative embodiment according to the disclosure depicted in FIG. 6, a dual-condenser arrangement may be provided at an overhead of a fractionation column. Crude methanol product may be separated from water and other heavy byproducts (if any) in the fractionation column (not shown), with an overhead stream 302 being conducted from the fractionation column to first and second condensers 312A, 312B. The overhead stream 302 may first be condensed to a first temperature in the first condenser 312A, with a portion of the overhead stream 302 being cooled in the first condenser 312A to a liquid state and a portion of the overhead stream 302 remaining in a gaseous state. The first condenser 312A may provide heat transfer through the medium of cooling water, refrigerant, or any other suitable medium introduced at a stream 311A and removed at a stream 313A.

The portion of the overhead stream 302 that remains in a gaseous state after being cooled in the first condenser 312A is conducted at a stream 304 to the reclaimer or second condenser 312B, where it may be cooled/condensed against a second medium introduced at a line 311B and removed at a line 313B. As with the first condenser 312A, the second condensing/cooling medium may comprise cooling water, refrigerant, or any other suitable medium provided in flow rates, temperatures, and pressures configured to effect a desired amount of condensation in the second condenser 312B.

The portion of the overhead stream 302 that was condensed to a liquid state in the first condenser 312A may be conducted at a stream 306 towards a stripping column 316. Similarly, the portion of the overhead stream 302 that was condensed to a liquid state in the second condenser 312B may be conducted at a stream 308 to the stripping column 316. The streams 306, 308 may be added to the stripping column 316 at a same height or different heights, or may be mixed together prior to being added to the stripping column 316. Owing to the amount of the overhead stream 302 that is condensed in the first condenser 312A, the second condenser 312B may be of reduced size relative to the first condenser 312A, providing capital expense reduction.

The embodiment of FIG. 6 may be arranged to operate in single-condenser mode or in dual-condenser mode. A valve 307 may be arranged on the stream 304 such that if the valve is closed, the system may operate in single-condenser mode wherein the gaseous portion of the overhead stream 302 exiting the first condenser 312A and the stripping gas exiting the stripping column 316 at stream 305 is vented via a stream 309, and may be disposed to recycle, atmosphere, or otherwise.

If the valve 307 is open, the system may operate in dual-condenser mode wherein the gaseous portion of the overhead stream 302 exiting the first condenser 314 at stream 304 and the stripping gas exiting the stripping column 316 at stream 305 is conducted to the second condenser 312B to be further condensed. A vent line 310 is provided to dispose gases remaining after overhead stream 302 and the stripping gas have been further condensed in the second condenser 312B to recycle, atmosphere, or otherwise.

The stripping column 316 may be formed as a packed column, with random packings 350 facilitating a greater surface area over which the liquid portions of the overhead stream 302 may be contacted with a stripping gas, such as $H_2$, $N_2$, or any other suitable stripping gas as discussed in previous embodiments. The stripping gas may be introduced via a line 314, which may be configured to enter the stripping column 316 near a bottom portion thereof, allowing the stripping gas to rise through the random packings 350 as the liquid portions of the overhead stream 302 fall downward through the stripping column 316, with the stripping gas provided in quantities, temperatures, and pressures suitable for effecting a desired separation of $CO_2$ entrained in the liquid portions of the overhead stream 302. In alternative embodiments, the stripping column 316 may be arranged as a trayed column or any other suitable configuration of separation unit, and with the stripping gas being fed to the stripping column 316 at any suitable location.

The stripping gas and stripped $CO_2$ and other gases may exit the stripping column 316 via a line 305, thereafter to join the line 304. Any entrained gases, including methanol, contained in the stripping gas exiting the stripping column 316 may be fed to the second condenser 312B to condense any entrained methanol product out of the stripping gas without condensing so much gas as to cause an undesirable degree of $CO_2$ entrainment in the liquid portion in the line 308.

Accordingly, the temperatures at which the first and second condensers 312A, 312B operate may be selected to optimize an amount of methanol condensed in the first and second condensers 312A, 312B without reducing the temperature of the overhead stream 302 and components thereof to a degree that entrains an undesired degree of $CO_2$ in the liquid products produced in the condensers 312A, 312B. Fluids that are not condensed to liquid and returned to the stripping column 316 are vented, recycled, or otherwise disposed via a line 310.

The liquid portion of overhead stream 302, now stripped of $CO_2$, may flow to a reflux drum 318, with a pump 320 operating to conduct the liquid portion of the overhead stream 302 either via a line 332 to the fractionation column as reflux, or via a valve 322 and a line 334 to a methanol product disposition. The amount of reflux may be determined based on the fractionation column, particularly based on a required reflux ratio.

In an alternative arrangement, the stripping gas may be provided at the reflux drum 318, with the stripping gas and stripped $CO_2$ arranged to flow upwards through a line connecting the reflux drum to the stripper column, with the liquid portion of the overhead product 302 flowing downward through the same line, with may be arranged for self-draining flow. The depicted embodiment is not limited, but rather the equipment, streams, and other components may be altered within the spirit and scope of the disclosure.

By providing a separations section comprising a fractionation column arranged with a stripping unit at the overhead product or stream, the process of purifying a methanol product stream is simplified and realizes capital and operational cost savings, as a dedicated light-ends fractionation column and associated equipment may be omitted. The stripping unit is able to effectively remove $CO_2$ and other components without the use of added heat and fractionation systems while realizing or in combination with thermodynamic enhancements.

Deuterated Methanol Production and Deuterium Recovery

In an alternative embodiment of the disclosure, the system for separating gas may be arranged to separate the byproducts of a deuterated methanol formation process. Deuterated methanol is gaining increasing attention as a precursor for intermediates in the preparation of deuterated drugs and is also a valuable solvent often used in nuclear magnetic resonance (NMR) spectroscopy, among other dispositions. Deuterium may be provided to a reactor as an alternative feedstock to hydrogen in the previously described Reactions 1 and 2, with a resulting formation from $CO_2$ and deuterium of deuterated methanol, deuterated ("heavy") water, unreacted feedstock, and other light-end byproducts. The system for separating gas may be modified to enable recovery and recycle of unreacted deuterium from the crude deuterated methanol in the reactor effluent, in particular by using a stripping tower at the overhead of a column according to the disclosure.

Heavy water recovered at the bottom of a fractionation column according to the disclosure may be processed in an electrolyzer to separate the heavy water into oxygen and deuterium. The deuterium may then be recycled as reactor feedstock, with mass controllers ensuring a proper ratio of reactants fed to the reactor. The fractionation column overhead products, including deuterated methanol, may be separated according to embodiments of the disclosure using a stripping column arranged at the overhead of the fractionation column to drive off $CO_2$ and other light-end byproducts and contaminants without the need for a dedicated light-ends column as described herein. The stripping gas may be $N_2$, $O_2$, steam, deuterium, or any other suitable gas.

The stripping gas and unreacted feedstock recovered from the crude methanol product therewith may be advantageously recycled as feedstock to the reactor, with the aforementioned mass controllers ensuring a proper ratio of reactants fed to the reactor.

Selection of Vapo-Condenser Heat Exchanger

The thermodynamic efficiency of the separation process is largely dependent on the efficiency of the exchange of heat in the vapo-condenser as depicted in the split tower embodiments of FIGS. 4 and 5, as the heat transfer efficiency is inversely related to the pressure required in the MP section of the separation column in order to provide sufficient reboiler duty for the LP section. The better the efficiency of heat transfer in the vapo-condenser, the lower the required pressure for the MP section so as to be sufficient to provide the reboiler duty for the LP section. Lower pressure in the MP section translates to better thermodynamic efficiency of separation (lower reboiler duty or mechanical vapor recompression work) and a lower capital cost (as the walls of the column may be less thick). As such there is a need for a heat exchange in vapo-condenser that maximizes the efficiency in order to minimize the operating pressure of the MP section.

Kettle-type reboilers, which are typical in existing processes, and which allow the transfer of large duties in a relatively compact design, typically have an approach temperature between the heating and cooling media of about 10° C. An approach temperature this large unfortunately leads to inefficient heat transfer and therefore lower efficiency and higher capital costs, as the pressure in the MP section needs to be higher in order to provide reboiler duty to the LP section. This results in a more expensive column (because thicker walls are required to contain the higher pressure) and increased reboiler duty required in the MP section to maintain the higher pressure and temperatures. Energy expenditures and as a result emissions are correspondingly increased.

In certain embodiments of the disclosure, the vapo-condenser of the split tower embodiments depicted in FIGS. 4 and 5 (110, 210, respectively) is not a kettle-type reboiler but is rather either a thermosiphon-type heat exchanger or a falling film evaporator-type heat exchanger. Thermosiphon-type heat exchangers or falling film evaporator-type heat exchangers serve to improve the thermodynamic efficiency in that the approach temperature in both (~1°) is lower than the approach temperature (~10°) in kettle-type reboilers. By decreasing the approach temperature, the required operating pressure of the MP section is reduced because the MP section need not reach the higher T required by an otherwise higher temperature approach. The resulting lower pressure of the MP section also reduces energy expenditures and emissions.

The use of thermosiphon-type or falling film evaporator-type heat exchangers thus advantageously addresses the problem of vapo-condensers not offering sufficiently close approach temperatures and optimizes the MP section operating conditions for greatest thermodynamic efficiency.

Reactor Design

Reactor design in methanol synthesis and in any chemical process is important for preserving catalyst life, for achieving acceptable product rate and quality, and for controlling process conditions. Existing methanol synthesis facilities typically comprise boiling water reactors which are expensive and complex but are required in order to handle large temperature peaks due to the exothermic nature of methanol synthesis.

Alternative reactors in existing methanol synthesis facilities typically comprise adiabatic or cold-shot reactors, which are less expensive than boiling water reactors but are inefficient and require the use of multiple reactors in order to achieve acceptable conversion rates. Existing facilities typically require a plurality of reactors, whether the reactors or boiling water reactors, adiabatic reactors, or a combination of boiling water reactor and adiabatic reactor.

Existing reactor designs, because of the high temperatures normally present in methanol synthesis and other exothermic processes further experience problems with catalyst sintering, wherein the normally crystalline catalyst reverts to its agglomerate state due to the high heat. Sintering reduces the effective life of the catalyst, leading to increased costs as the facility and process must be interrupted to allow for the catalyst to be removed, regenerated, and replaced, or alternatively increases costs as redundant reactor systems must be installed to allow for catalyst swap out without shutting down the facility.

Existing reactor designs often comprise a hollow section in the center of the reactor which is used to structurally support the weight of the catalyst, e.g. by providing additional mechanical structures or supports. This unfortunately has the effect of unevenly distributing the catalyst, reactants, and cooling tubes (in tube cooled reactors).

Accordingly, there is a need for a reactor (and reaction suite) that allows for the use of a single tube-cooled reactor to minimize capital costs, technical complexity (and thus maintenance costs and down-time), and operating expenses.

The above problems are addressed by the selection of Reactions 1 and 2 to synthesize methanol, which results in a lower heat profile than existing methanol synthesis reaction suites. As a result of the lower heat profile, a boiling water reactor is not required in order to control the temperature of the reactor. A tube-cooled reactor is therefore sufficient to control the temperature resulting from the Reactions 1 and 2. Moreover, a single tube-cooled reactor is sufficient to produce the desired methanol product as it is more efficient than adiabatic reactors due to its lower operating temperature, and multiple reactors in series are not required for sufficient conversion. Thus by selecting Reactions 1 and 2, a single tube-cooled reactor may advantageously be used to achieve desired methanol production.

Figure 7:
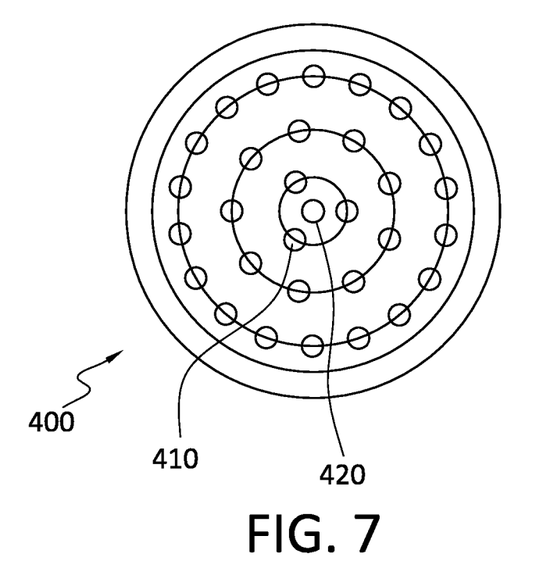
FIG. 7 is a plan view of a catalyst support tray according to an embodiment of the separations system.

In an embodiment of the disclosure depicted in FIG. 7, a cross-section of a reactor 400 for converting $CO_2$ into methanol is shown. In an improved design of a tube-cooled reactor, new tubes 410 are added to the catalyst support plate 420. The addition of the tubes 410 help to distribute heat more effectively and consistently in the reactor 400. The more even heat distribution prevents hot spots and thus minimizes catalyst sintering, thereby extending the useful life of the catalyst between regenerations.

Figure 8:
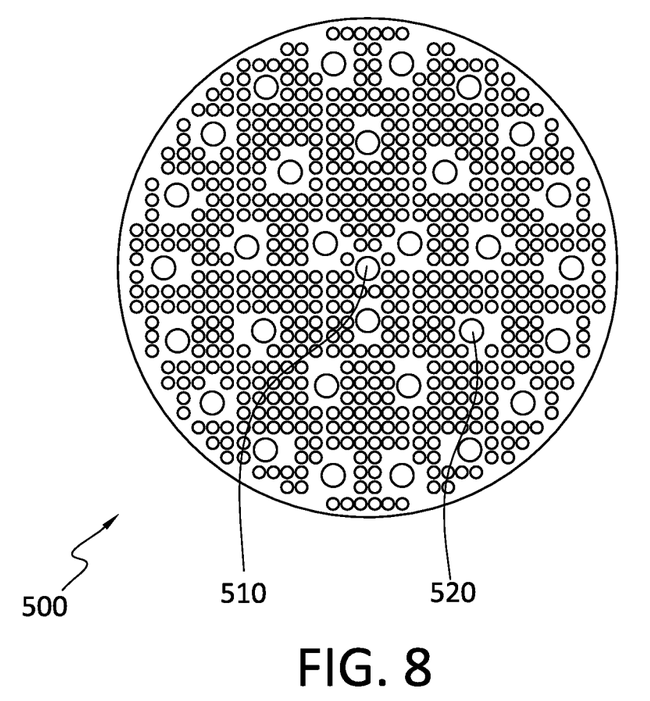
FIG. 8 is a plan view of a catalyst bed according to an embodiment of the separations system.

In another embodiment of the disclosure depicted in FIG. 8, an improved catalyst bed 500 is provided, with tubes 510 running through the catalyst bed in an even distribution to create an even heat distribution. Perforations 520 additionally provide for even catalyst mixing.

It is to be understood that not necessarily all objects or advantages may be achieved under any embodiment of the disclosure. Those skilled in the art will recognize that the system for separating gas including $CO_2$ may be embodied or carried out in a manner that achieves or optimizes one advantage or group of advantages as taught without achieving other objects or advantages as taught or suggested.

The skilled artisan will recognize the interchangeability of various disclosed features. Besides the variations described, other known equivalents for each feature can be mixed and matched by one of ordinary skill in this art to make or use a system for removing light gases under principles of the present disclosure. It will be understood by the skilled artisan that the features described may be adapted to other types of chemical species and processes. Hence this disclosure and the embodiments and variations thereof are not limited to methanol synthesis processes or to removing $CO_2$, but rather can be utilized in any chemical process wherein removing a gas species is desired or required.

Although this disclosure describes certain exemplary embodiments and examples of system for removing gas, it therefore will be understood by those skilled in the art that the present disclosure extends beyond the specifically disclosed embodiments to other alternative embodiments and/or uses of the disclosure and obvious modifications and equivalents thereof. It is intended that the present disclosure should not be limited by the particular disclosed embodiments described above.

The invention claimed is:

1. A system for separating a gas from a process stream, the system comprising:
   a separation unit configured to receive the process stream of a chemical process and to separate at least one component of the process stream, the separation unit comprising a first heat exchanger located at an overhead portion of the separation unit and receiving an overhead stream of the process stream from the overhead portion of the separation unit, the first heat exchanger being configured for condensing at least a portion of the overhead stream of the process stream; and
   a stripper unit configured to receive the condensed portion of the overhead stream of the process stream from the first heat exchanger and configured for separating the gas from the condensed portion of the overhead stream of the process stream by introducing at least one stripping fluid thereunto;
   wherein the chemical process is a process that synthesizes methanol from syngas.

2. The system for separating a gas from a process stream of claim 1, wherein the process stream comprises $CO_2$, water, and methanol.

3. The system for separating a gas from a process stream of claim 1, wherein the at least one stripping fluid comprises gaseous $N_2$ or $H_2$.

4. The system for separating a gas from a process stream of claim 1, wherein at least one waste gas stream comprising a portion of the at least one stripping fluid and a portion of the separated gas is generated.

5. The system for separating a gas from a process stream of claim 4, wherein the at least one waste gas stream is scrubbed of entrained methanol before venting to atmosphere.

6. The system for separating a gas from a process stream of claim 1, wherein the stripper unit comprises a gas sparger.

7. The system for separating a gas from a process stream of claim 1, further comprising a drum configured for receiving the condensed overhead stream from the first heat exchanger upstream of the stripper unit.

8. The system for separating a gas from a process stream of claim 7, wherein the drum is a reflux drum connected to the separation unit and configured to accumulate the condensed portion of the process stream.

9. The system for separating a gas from a process stream of claim 8, further comprising a waste gas stream generated at the stripper unit.

10. The system for separating a gas from a process stream of claim 8, wherein the stripper unit is integral with the reflux drum, and the at least one stripping fluid is introduced to the condensed overhead stream within the reflux drum.

11. The system for separating a gas from a process stream of claim 8, wherein the stripper unit is integral with the reflux drum, and the at least one stripping fluid is introduced to the condensed overhead stream within the stripper unit.

12. The system for separating a gas from a process stream of claim 1, wherein the separation unit is a split column comprising a relatively high-pressure column and a relatively low-pressure column, the system further comprising a second heat exchanger, each of the relatively high-pressure and low-pressure columns further comprising a respective one of the first and second heat exchangers.

13. The system for separating a gas from a process stream of claim 7, wherein a reflux stream and a non-reflux stream extend and flow downstream from the drum, and the stripper unit receives the non-reflux stream as the condensed overhead stream and the separation unit receives the reflux stream.

14. A system for separating a gas from a process stream, the system comprising:
   a separation unit configured to receive a process stream of a chemical process and to separate at least one component of the process stream, the separation unit comprising a first heat exchanger located at an overhead portion of the separation unit and receiving an overhead stream of the process stream from the overhead portion of the separation unit, the first heat exchanger being configured for condensing at least a portion of the overhead stream of the process stream; and
   a stripper unit configured to receive the condensed portion of the overhead stream of the process stream from the first heat exchanger and being configured for separating the gas from the condensed portion of the overhead stream of the process stream by introducing at least one stripping fluid thereunto;
   wherein at least one waste gas stream comprising a portion of the at least one stripping fluid and a portion of the separated gas is generated;
   wherein the at least one waste gas stream is generated from the stripper unit and is recycled to upstream of the chemical process.

15. A system for separating a gas from a process stream, the system comprising:
   a separation unit configured to receive a process stream of a chemical process and to separate at least one component of the process stream, the separation unit comprising a first heat exchanger located at an overhead portion of the separation unit and receiving an overhead stream of the process stream from the overhead portion of the separation unit, the first heat exchanger being configured for condensing at least a portion of the overhead stream of the process stream; and
   a stripper unit configured to receive the condensed portion of the overhead stream of the process stream from the first heat exchanger and being configured for separating the gas from the condensed portion of the overhead stream of the process stream by introducing at least one stripping fluid thereunto;
   wherein at least one waste gas stream comprising a portion of the at least one stripping fluid and a portion of the separated gas is generated;
   wherein the at least one stripping fluid is a reactant of the chemical process.

16. A method for separating a gas from a process stream, the method comprising the steps of:
   providing a separation unit configured to receive a process stream of a chemical process and to separate at least one component of the process stream,
   providing a heat exchanger at an overhead portion of the separation unit, the heat exchanger being configured for condensing at least a portion of an overhead stream of the process stream; and
   providing a stripper unit configured to receive the condensed portion of the overhead stream of the process stream from the heat exchanger, the stripper unit separating a gas from the condensed portion of the overhead stream by introducing at least one stripping fluid thereto;
   wherein the chemical process is a process that synthesizes methanol from syngas.

17. The method for separating a gas from a process stream of claim 16, further comprising the steps of:
  feeding the process stream to the separation unit;
  separating the process stream into the overhead stream and a bottom portion;
  condensing the portion of the overhead stream using the heat exchanger; and
  separating the gas from the condensed portion of the overhead stream by introducing the at least one stripping fluid to the stripper unit.

18. The method for separating a gas from a process stream of claim 16, wherein the heat exchanger comprises first and second heat exchangers, the first heat exchanger being configured to condense the portion of the overhead stream, and the second heat exchanger being configured to receive a gaseous stream from the first heat exchanger and to condense a portion of the gaseous stream from the first heat exchanger.

* * * * *